(12) United States Patent
Litwin et al.

(10) Patent No.: US 6,319,722 B1
(45) Date of Patent: Nov. 20, 2001

(54) ANALYSIS OF HYDROGEN SULFIDE IN HYDRIDE GASES

(75) Inventors: Michael Mark Litwin, Cheektowaga; Sateria Salim, Amherst; John Burnham Goddard, Grand Island, all of NY (US)

(73) Assignee: Praxair Technology, Inc., Danbury, CT (US)

( * ) Notice: Subject to any disclaimer, the term of this patent is extended or adjusted under 35 U.S.C. 154(b) by 0 days.

(21) Appl. No.: 09/275,574

(22) Filed: Mar. 24, 1999

(51) Int. Cl.$^7$ .......................... G01N 33/00; G01N 21/75
(52) U.S. Cl. ...................... 436/121; 436/43; 436/44; 436/103; 436/119; 436/166; 436/169
(58) Field of Search ................. 422/62, 86, 87, 422/91; 436/43, 44, 119–121, 166, 169 103

(56) References Cited

U.S. PATENT DOCUMENTS

| | | | |
|---|---|---|---|
| 2,232,622 | 2/1941 | Moses et al. | 23/255 |
| 2,551,281 | 5/1951 | Moses et al. | 23/255 |
| 2,800,397 | 7/1957 | Offutt et al. | 23/232 |
| 2,895,807 | 7/1959 | Sorg et al. | 23/255 |
| 3,464,799 | 9/1969 | Kimbell | 23/254 |
| 4,032,297 | * 6/1977 | Lyshkow | 422/91 |
| 4,127,780 | 11/1978 | Kimbell | 250/559 |

FOREIGN PATENT DOCUMENTS

| | | | |
|---|---|---|---|
| 116383 | * 8/1984 | (EP) | . |
| 1438625 | 4/1965 | (FR) | . |
| 1539930 | * 9/1968 | (FR) | . |
| 5-10938 | * 1/1993 | (JP) | . |
| 5-34291 | * 2/1993 | (JP) | . |
| 6-186221 | * 7/1994 | (JP) | . |
| 8-178910 | * 7/1996 | (JP) | . |

OTHER PUBLICATIONS

W. Sui et al, J. Air Pollut. Contr. Assoc. 1971, 21, 636–638, Oct. 1971.*
B. A. Larson ISA 1991, 25, 129–148.*
A. Fensom et al, Analyst 1971, 96, 194–200, Mar. 1971.*
K. Beckers TU 1988, 29, M20–M23, Mar. 1988.*
R. narayanaswamy et al, Analyst 1988, 113, 661–663, Apr. 1988.*
T, Tanaka et al, Anal. Sci. 1992, 8, 627–630, Oct. 1992.*
Y. Hayakawa et al, Anal. Sci. 1995, 11, 657–661, Aug. 1995.*

* cited by examiner

*Primary Examiner*—Arlen Soderquist
(74) *Attorney, Agent, or Firm*—Blake T. Biederman

(57) ABSTRACT

The method measures hydrogen sulfide concentrations in hydride gases in a sealed vessel. The sealed vessel has a gas inlet to receive a stream of hydride gas, a gas outlet to remove the stream of hydride gas and a metal acetate substrate. The stream of hydride gas contains a concentration of hydrogen sulfide gas. Introducing the stream of hydride gas through the gas inlet contacts the acetate substrate with the stream of hydride gas. Reacting the hydrogen sulfide gas contained in the stream of hydride gas with the acetate substrate modifies optical properties of the acetate substrate. Then measuring the optical properties of the acetate substrate determines the concentration of the hydrogen sulfide gas contained in the stream of hydride gas.

11 Claims, 3 Drawing Sheets

ANALYSIS OF HYDROGEN SULFIDE IN HYDRIDE GASES

BACKGROUND OF THE INVENTION

Phosphine is a reagent used in the manufacture of light emitting devices (LEDs) by metal-organic chemical vapor deposition (MOCVD) techniques. For example, manufacturers use phosphine to produce AlInGaP (aluminum indium gallium phosphide) LEDs. Unfortunately, sulfur in the high parts per billion (ppb) or low parts per million (ppm) ranges adversely impacts LED properties. For example, even high purity phosphine starting materials can contribute to this sulfur contamination. Hydrogen sulfide is the most common source of this contamination. In order to eliminate this source of contamination, gas manufacturers require an analytical method for measuring hydrogen sulfide ($H_2S$) in phosphine ($PH_3$) on the order of 100 parts ppb or lower to improve the product by purification.

Extrapolating the semiconductor sulfur analysis back to the phosphine gas is not acceptable as a quality control or product monitoring for a phosphine plant. This process is expensive and highly resource-intensive. Total sulfur analyzers based on reduction to $H_2S$ in hydrogen cannot be used because $PH_3$ would decompose on the catalyst at the reduction temperatures required. Furthermore, analyzing total sulfur by oxidation in oxygen to $SO_2$ would be hazardous, because of the flammability of $PH_3$.

Gas chromatography provides a problematic technique for measuring trace $H_2S$ levels in hydride gases. This technique, while theoretically possible, is impracticable because separating trace $H_2S$ from streams of approximately 100 percent $PH_3$ is difficult due to the closeness of the elution times and "stickiness" of the $H_2S$. Furthermore, $PH_3$ also interferes with the signal from trace $H_2S$ sensors.

Finally, as far as known, lead acetate paper tape analyzers have never been used with $PH_3$ service or in the presence of any toxic or spontaneously flammable gas. (Phosphine is extremely toxic, with a TLV—threshold limit value—of 300 ppbv, and gives no odor warning at the TLV. It is also spontaneously flammable in air.) Furthermore, commercial lead acetate paper tape analyzers are unsuitable, since they are not designed with leak-tight components. In "Gas Analysis and Testing of Gaseous Materials", American Gas Association, Inc., N.Y., c1945 (pp.148, 277–278), V. J. Altieri describes a qualitative test for hydrogen sulfide in gases using a filter paper strip soaked in 5 percent lead acetate solution. The process visually compares the darkness of the paper to paper not exposed to the gas. D. V. Moses et al. in "$H_2S$ Recorder", U.S. Pat. No. 2,232,622, describe a lead acetate paper tape analyzer. An illuminating gas passes through the tape that is drawn through a roller at a fixed rate. The darkness of the stain is read optically with reflected light to a photocell and compared with unexposed tape. This is an early example of instrumentation for determining $H_2S$ with a lead acetate tape method. Similarly, Moses et al. (DuPont), in "Automatic Gas Analyzer" in U.S. Pat. No. 2,551,281, disclose an improvement of the above invention. This analyzer humidifies the gas and controls both tape movement and exposure time.

Offutt et al. (Standard Oil), in "Method and Apparatus for Analyzing a Reactive Gas", U.S. Pat. No. 2,800,397, disclose an instrument that analyzes air that does not pass through the tape. The instrument uses transmitted light, rather than reflected light, to measure the tape darkening or $H_2S$. This instrument humidifies an air sample at a constant temperature. Furthermore, in "Multiple Stream Gas Analyzer", U.S. Pat. No. 2,895,807, Sorg et al. teach humidifying a tape at a relative humidity of 30–50 percent, using a saturated sodium chromate solution. In this process, a sample's gas stream humidifies the tape.

American Society for Testing and Materials, "Standard Test Method for Hydrogen Sulfide in the Atmosphere by Rate of Change of Reflectance", ASTM D4323-84, 1984, established the standard method for determining $H_2S$ in air. This standard uses a Houston-Atlas lead acetate paper tape analyzer to measure $H_2S$ in the range of 1–3000 ppbv.

Kimbell, in "Gas Detector", U.S. Pat. No. 3,464,799, describes a technique for using an analyzer in explosive environments. Finally, Kimbell, in "Periodic Sampling Concentration Indicator", U.S. Pat. No. 4,127,780, describes the operation of the Houston-Atlas lead acetate tape hydrogen sulfide analyzer. This process relies on an electronic differentiating circuit to measure darkening rate. The process can determine darkening rate in a period that is substantially linear with hydrogen sulfide concentration.

Unfortunately, these lead acetate analyzers are unsuitable for measuring hydrogen sulfide in hydride gases such as, phosphine. These devices, constructed without leak-tight components are unsuitable because of phosphine's toxicity and spontaneous flammability in air. Furthermore, these devices add moisture to the test cell itself. This moisture could combine with phosphine to form difficult to remove aqueous phosphine solutions. These solutions can decompose or outgas toxic phosphine.

It is an object of this invention to measure hydrogen sulfide in parts per billion in hydride gases.

It is a further object of this invention to moisten a metal acetate tape with water in a controlled manner.

It is a further object of this invention to measure hydrogen sulfide in an accurate and reliable manner.

SUMMARY OF THE INVENTION

The method measures hydrogen sulfide concentrations in hydride gases in a sealed vessel. The sealed vessel has a gas inlet to receive a stream of hydride gas, a gas outlet to remove the stream of hydride gas and a metal acetate substrate. The stream of hydride gas contains a concentration of hydrogen sulfide gas. Introducing the stream of hydride gas through the gas inlet contacts the acetate substrate with the stream of hydride gas. Reacting the hydrogen sulfide gas contained in the stream of hydride gas with the acetate substrate modifies optical properties of the acetate substrate. Then measuring the optical properties of the acetate substrate determines the concentration of the hydrogen sulfide gas contained in the stream of hydride gas.

The apparatus for measuring hydrogen sulfide concentrations in gas streams includes a sealed vessel having a gas inlet for receiving a stream of hydrogen sulfide-containing gas and a gas outlet for discharging the stream of hydrogen sulfide-containing gas. A test cell within the vessel connects to the gas inlet and the gas outlet, the test cell is for reacting the stream of hydrogen sulfide-containing gas received from the gas inlet with a metal acetate substrate and for modifying optical properties of the acetate substrate. A purge chamber connected to the test cell has an inlet for receiving an inert gas and an outlet for removing the inert gas. An optical sensor measures the modified optical properties of the acetate substrate and determines the hydrogen sulfide gas concentration.

BRIEF DESCRIPTIONS OF THE DRAWINGS

DETAILED DESCRIPTION

The improved design for hydrides such as $PH_3$ includes a tape box isolated from the electronics. This enables sealing and purging of the box with all of the purge gas directed to a phosphine scrubber. The design also uses a humidified purge gas that prevents the metal acetate substrate from drying out. The process operates with metal acetate deposited on any substrate. Most advantageously, the substrate consists of a tape. The humidified purge gas moistens the metal acetate to facilitate the darkening reaction with the metal acetate. Advantageously, the metal acetate is an element selected from the group consisting of lead and zinc.

An optional improvement in this design is to direct the humidified stream at the lead acetate tape to provide a constant-humidified flow. This eliminates any requirement to rely on diffusion of moisture from remote parts of the tape box. Since the design's sample gas stream does not humidify the metal acetate, it allows the sample gas stream to flow directly to the tape without passing through a bubbler or other humidifying device. In this way, the sample gas remains dry. For example, phosphine usually contains less than about 1 ppm water. This also has the advantage that the process produces no aqueous phosphine solutions—long after analyzing hydrogen sulfide content, residual phosphine solutions have the potential to decompose or to outgas toxic phosphine.

Figure 1:
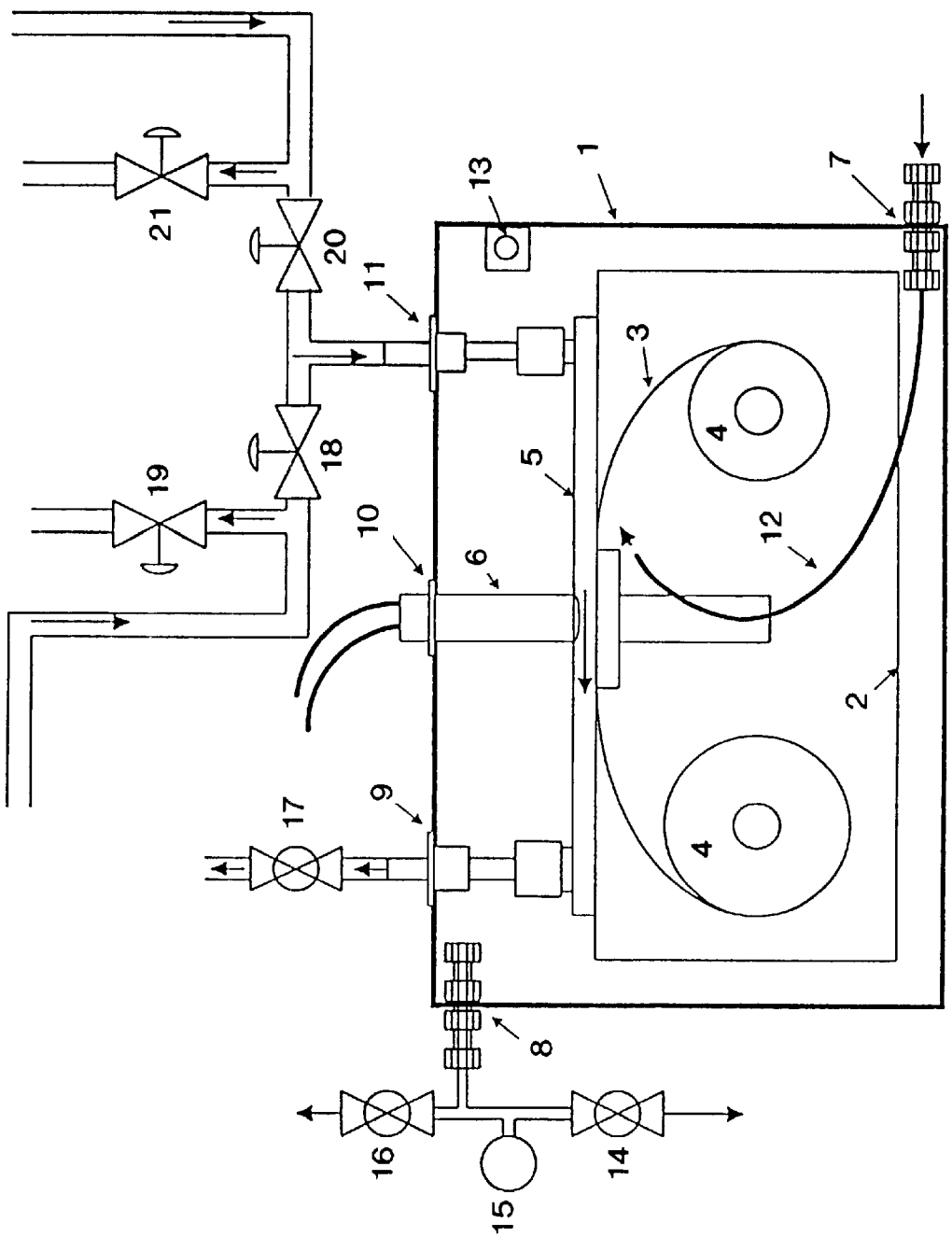
FIG. 1 is a schematic drawing of a metal acetate tape device for measuring $H_2S$ in hydride gases.

Referring to FIG. 1, the phosphine gas handling system is separated from the electronics (not shown). A lead acetate tape box 2 is placed inside a stainless steel NEMA 4X sealed purge box 1. The tape box 2 contains a roll of lead acetate impregnated or coated tape 3, mechanized tape advance spools 4, a gas sample test cell 5, and a fiber optic sensor assembly 6. The white lead acetate tape 3 turns brown with exposure to $H_2S$. The purge box 1 contains gas tight entry and exit ports (at 7, 8, 9, 10 and 11). In particular, the purge box contains a humidified nitrogen purge gas inlet 7, a purge gas outlet 8, a sample gas outlet 9, a fiber optic sensor entrance 10, a sample gas inlet 11, a humidified purge gas direction tube 12 and a lid safety switch 13. Most advantageously, the purge box has two sealed entrance and exit ports (not illustrated) for the tape drive and safety lid switch. A purge outlet manifold, connected to the purge box at purge gas outlet 8 contains a pressure gage 15, a purge gas monitoring valve 16 and a vent scrubber isolation valve 14. The sample gas outlet 9 also has a scrubber isolation valve 17. The sample and calibration gas feed manifold utilizes four pneumatically actuated diaphragm valves 18, 19, 20, and 21 to direct the flow to the cell or to the scrubber vent.

Figure 2:
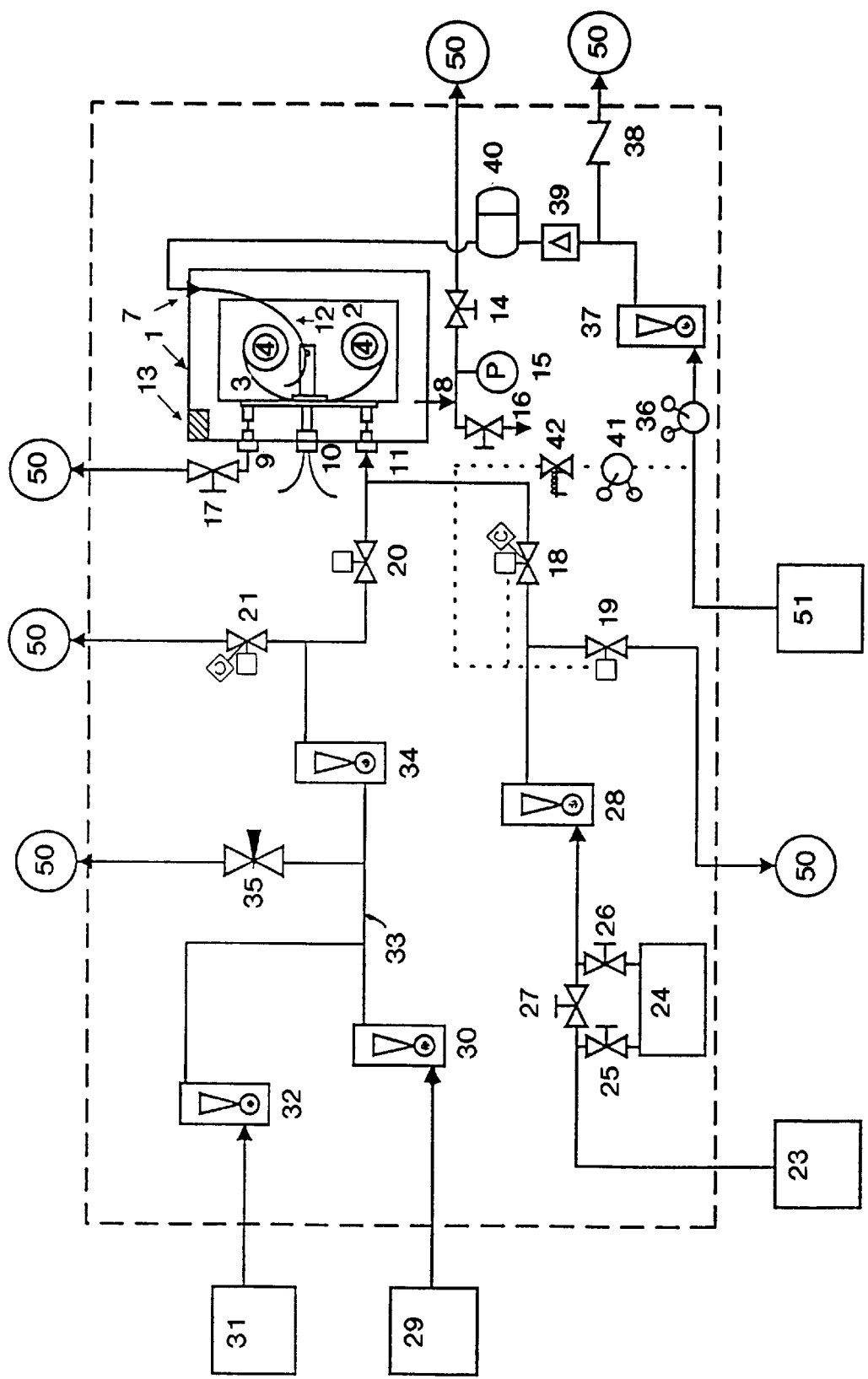
FIG. 2 is a gas flow schematic of the sample and calibration system.

Referring to FIG. 2, the phosphine delivery system consists of a regulated $PH_3$ source 23 that feeds a $PH_3$ purifier 24 through a valve manifold consisting of inlet, outlet, and bypass valves 25, 26, and 27, respectively. The $PH_3$ flow to valves 18 and 19 is controlled with a flowmeter 28. Optionally, the apparatus substitutes the flowmeters with mass flow controllers for improved accuracy. The calibration gas is prepared by: 1) metering a regulated $H_2S$-in- nitrogen standard 29 through a flowmeter 30; and 2) blending it thorough calibrated gas supply line 33 with a regulated nitrogen diluent source 31 controlled with a flowmeter 32. The resulting blend is measured with an additional flowmeter 34 as it passes to the analyzer through the valve 20 or vents through the valve 21. Excess calibration blend is vented through a discharge valve 35. All vents, such as vent 38 are directed to a gas scrubber system 50. A regulator 36 and flowmeter 37 regulate a nitrogen purge gas source 51 through a flow switch 39 and a humidifier 40. The nitrogen source 51 also serves as the pneumatic actuator supply for valves 18 and 19. The nitrogen source 51 is delivered through a regulator 41 and electrically controlled by a solenoid 42. Another optional modification is to make the delivery system and tape box gas tight so that both sample and purge gases can be directed essentially completely to a phosphine scrubber for safe disposal.

Figure 3:
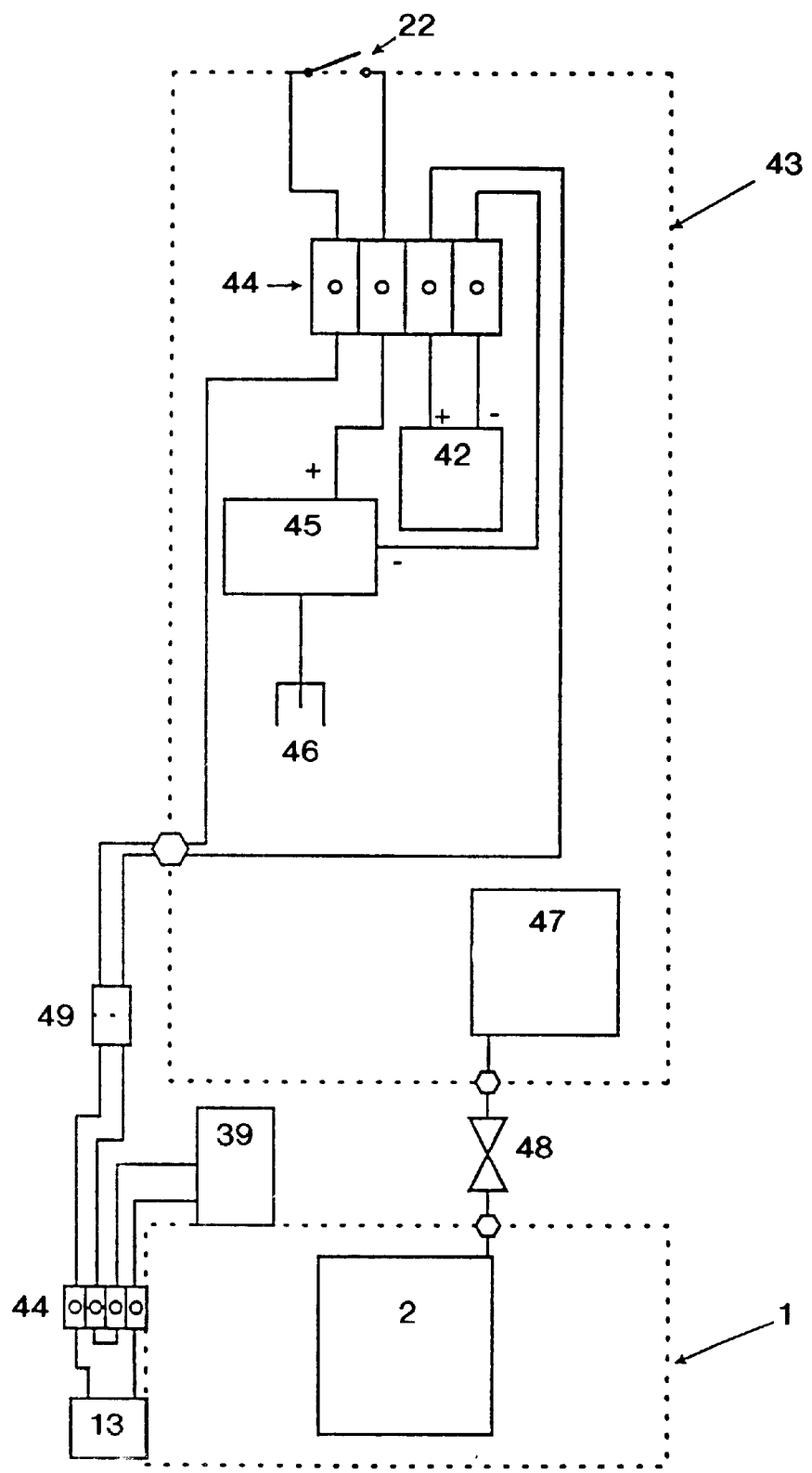
FIG. 3 is an electrical schematic of the safety system.

Referring to FIG. 3, an electronics compartment 43 is electrically connected to purge box 1 with electrical connectors 48 and 49. Wires are terminated at terminal blocks 44. Other components of the electronics compartment 43 are a 12-volt DC power supply 45, a 120-volt AC main power supply 46, and a tape advance motor power supply 47. The safety system is designed to stop the flow of phosphine to the analyzer and to direct it to vent by closing the valve 18 and opening the valve 19 (FIGS. 1 and 2). This occurs upon the following: (a) the lid to the sealed purge box 1 is opened (opening the safety switch 13); (b) the nitrogen purge gas flow through the flow switch 39 drops below a preset value, e.g., 5 Liters/minute; (c) the pneumatic valve actuator pressure falls below a factory preset value, e.g. 40 psig; or (d) the manual toggle switch 22 is opened (turned to "OFF" position).

EXAMPLE 1

Phosphine from a cylinder was passed through a specially prepared $H_2S$ absorption unit to remove hydrogen sulfide. The purified phosphine was then analyzed by the standard addition method with the modified lead acetate paper tape analyzer described in FIGS. 1–3. The method utilized a seven-minute tape equilibration time with the 90 percent phosphine-10percent nitrogen-$H_2S$ blend, followed by a seven-minute read time. The equilibration time facilitated making subsequent optical darkness readings more linear with $H_2S$ concentration.

When testing with no standard addition of $H_2S$, a value of zero ppb was found (i.e., the tape did not darken at all). Then a 10 percent (by volume) nitrogen stream containing $H_2S$ was added to give the phosphine 200 ppb $H_2S$. The resultant reading was 202 ppb $H_2S$. This indicated that the phosphine contributed little to the darkness reading.

EXAMPLE 2

Phosphine from a cylinder was analyzed by the standard addition method to determine the $H_2S$ content. The tape calibration, equilibration and read method were the same as in Example 1. Table 1 below provides the results of this method.

TABLE 1

| Standard Addition (ppb $H_2S$) | Beginning Darkness | Final Darkness | Change in Darkness | Ppb $H_2S$ Displayed | Ppb $H_2S$ from Phosphine Sample |
|---|---|---|---|---|---|
| 0.00 | 26.03 | 26.18 | 0.15 | 1.63 | — |
| 150.00 | 29.30 | 40.53 | 11.23 | 182.86 | 32.86 |
| 200.00 | 33.46 | 47.82 | 14.36 | 234.42 | 34.42 |

The beginning darkness was an optical readout expressed as percentage darkening at the beginning of the read period; and the final darkness was the readout at the end of the seven-minute read period. When no standard addition of H$_2$S was made, the tape darkened very little, indicating that the concentration was low and that a standard addition must be made to bring the darkness level into the linear range. When 150 or 200ppb H$_2$S was added, sufficient to bring the tape reading into the linear range, the darkness change indicated a level of 183 and 234 ppb H$_2$S, respectively. Since this was 33–34 ppb above the level of the standard addition, the phosphine contributed 33–34 ppb. Therefore, since the nitrogen diluted the sample by 10 percent, the H$_2$S in the original cylinder phosphine contained 37–38 ppb H$_2$S.

It is possible to construct the analyzer with components from a lead acetate paper tape hydrogen sulfide analyzer, such as a Houston Atlas analyzer. The Houston Atlas analyzer contains components that monitor the rate of darkening of the tape or the final darkness count over a specific period with fiber optics. Furthermore, in this design, the sample gas flows over (not through) the tape. The apparatus however operates with any method that could detect the darkening of a metal acetate tape with H$_2$S. In some designs, transmitted light could be monitored, or the gas could be passed through the tape rather than over the tape. When testing however, it is important to use a metal acetate tape prepared in a consistent manner. Other lead acetate tape H$_2$S analyzers and air monitors are commercially available, e.g. from Trace Environmental, Del Mar Scientific, and MDA Scientific. The most important modifications are to isolate the gas delivery system and tape from the electronics so that the tape box can be purged and humidified with an inert gas stream, preferably nitrogen or argon.

The process can improve its sensitivity by increasing the tape exposure time (both equilibration and read times). This allows a lower H$_2$S concentration in the standard addition (or even no standard addition if enough H$_2$S is in the sample). Furthermore, controlling the humidity at higher levels could improve sensitivity.

Optionally, adding moisture to the purge gas can be accomplished simply by bubbling it through water or by passing it over water. It is most advantageous to direct the humidified purge gas onto the lead acetate tape at a point before it advances into the sample exposure position. The purge flow rate should be sufficient to maintain the purge box essentially free of air, but otherwise is not critical (the test used about 10 Liters/minute).

A preferred mode of operation is to calibrate by standard additions. In this method, hydrogen sulfide as a dilute standard in nitrogen (or argon) is blended into the actual phosphine sample. This internal standard is delivered preferably in ratios such that the phosphine is not diluted to less than 75 percent of its original concentration. The process typically operated at 90 percent PH$_3$—10 percent N$_2$ standard containing H$_2$S. By using internal standards, the process can calculate the H$_2$S in the phosphine sample without actually having a pre-made standard of H$_2$S in PH$_3$.

The optical readings of the brown lead sulfide stain are substantially linear with H$_2$S concentration within a certain concentration range. This substantially linear range consists of an area whose linear extrapolation introduces less than ten percent error in the result. The linear range is also the most sensitive range. [Below or above this range, the readings are nonlinear.] Thus, it is most advantageous to be within this range when analyzing a sample. The linear range will vary with conditions chosen, for example the time of tape exposure, flow rate, humidity, temperature, among other factors. Advantageously, the measuring of the darkened lead acetate substrate or tape consists of an initial exposure to a stream of phosphine gas for 1 to 30 minutes and a second exposure of 1 to 30 minutes to measure the change in optical properties or H$_2$S concentration. Typically, operating with a tape exposure time of 14 minutes (seven minutes equilibration, seven minutes optical read time), 150 mL/min flow rate, 20 percent relative humidity, and ambient temperature produced reliable ppb measurements.

The optimum range for linear measurement of H$_2$S is approximately 100–250 ppbv for lead acetate tape. If samples are in this range, they do not require standard additions to provide reliable measurements. Industry demands however require measurement of lower H$_2$S levels. For example, some commercial processes require H$_2$S levels to be below 50 ppb. At these low levels, it is preferable to add a calibrated primer gas and use the standard addition method. Furthermore, it is also possible to use the nonlinear portion of the H$_2$S calibration curve for measurements below 100 ppb without making standard additions. For H$_2$S levels below about 50 ppb however, the tape darkness reading changes so little (for the 14-minute exposure time) that sensitivity and accuracy of the readings are poor.

For phosphine samples with unknown ranges of hydrogen sulfide, it is preferable to run the sample first without a standard addition of hydrogen sulfide to determine what (if any) standard addition is required to bring the darkness reading within the linear range of the analyzer.

The process of the invention operates to measure hydrogen sulfide in hydride gases such as phosphine, arsine (AsH$_3$), silane (SiH$_4$) and germane (GeH$_4$). Since some hydrides such as arsine can react with lead acetate however, the process may require a different metal acetate tape that is non-reactive. Optionally, it may be possible to control test conditions to ensure that the metal acetate tape does not react with the hydride.

The device and method of the invention provide for accurate and reliable testing of H$_2$S in hydride gases. Most advantageously, the process measures hydrogen sulfide present in a phosphine gas. It measures H$_2$S in this gas in the parts per billion range. Moistening the metal acetate tape with a separate purge gas allows for measurement without humidity fluctuations associated with air.

Although the invention has been described in detail with reference to certain preferred embodiments, those skilled in the art will recognize that there are other embodiments of the invention within the spirit and the scope of the claims.

We claim:

1. A method of measuring hydrogen sulfide concentrations in hydride gases comprising the steps of:

a) providing a sealed vessel, said vessel having a gas inlet to receive a stream of hydride gas, a gas outlet to remove said stream of hydride gas and a metal acetate substrate, said metal acetate being selected from the group consisting of lead acetate and zinc acetate and said stream of hydride gas containing a concentration of hydrogen sulfide gas;

b) exposing said acetate substrate to a calibrated hydrogen sulfide-containing primer gas to pre-darken said acetate substrate;

c) introducing said stream of hydride gas through said gas inlet to contact said acetate substrate with said stream of hydride gas;

d) reacting said hydrogen sulfide gas contained in said stream of hydride gas with said acetate substrate to modify optical properties of said acetate substrate; and e) measuring said optical properties of said acetate substrate to determine said concentration of said hydrogen sulfide gas contained in said stream of hydride gas with a substantially linear relationship between said hydrogen sulfide gas and darkness of said acetate substrate.

2. The method of claim 1 including the additional step of purging said vessel with an inert gas.

3. The method of claim 1 including the additional step of purging said vessel with a mixture of an inert gas and water vapor to moisten said acetate substrate before said reacting of said hydrogen sulfide gas with said acetate substrate.

4. The method of claim 1 wherein said measuring includes comparing a darkened acetate substrate to a standard, said standard being prepared from a known hydrogen sulfide concentration.

5. The method of claim 1 wherein said acetate substrate consists of a lead acetate tape and said lead acetate tape darkens by browning upon exposure to said hydrogen sulfide gas.

6. A method of measuring hydrogen sulfide concentrations in phosphine gases comprising the steps of:
   a) providing a sealed vessel, said vessel having a gas inlet to receive a stream of phosphine gas, a gas outlet to remove said stream of phosphine gas and a lead acetate substrate, said stream of phosphine gas containing a concentration of hydrogen sulfide gas;
   b) introducing said stream of phosphine gas through said gas inlet to contact said lead acetate substrate with said stream of phosphine gas;
   c) reacting said hydrogen sulfide gas contained in said stream of phosphine gas with said lead acetate substrate to darken said lead acetate substrate; and
   d) measuring said darkened lead acetate substrate to determine said concentration of said hydrogen sulfide gas contained in said stream of phosphine gas.

7. The method of claim 6 including the additional step of purging said vessel with an inert gas.

8. The method of claim 6 including the additional step of purging said vessel with a mixture of an inert gas and water vapor to moisten said lead acetate substrate before said reacting of said hydrogen sulfide gas with said lead acetate substrate.

9. The method of claim 6 including the additional step of exposing said lead acetate substrate to a calibrated hydrogen sulfide-containing primer gas before said introducing of said stream of phosphine gas to pre-darken said lead acetate substrate and to allow said measuring of said optical properties of said lead acetate substrate with a substantially linear relationship between said concentration of said hydrogen sulfide gas and darkness.

10. The method of claim 6 wherein said measuring includes comparing a darkened lead acetate substrate to a standard, said standard being prepared from a known hydrogen sulfide concentration.

11. The method of claim 6 wherein said measuring of said darkened lead acetate consists of measuring darkness of said lead acetate substrate after an initial exposure to said stream of phosphine gas for a period of about 1 to 30 minutes and after a second exposure to said stream of phosphine gas for a period of about 1 to 30 minutes to measure change in optical properties of said lead acetate substrate.

\* \* \* \* \*